(12) United States Patent
Sun et al.

(10) Patent No.: US 8,992,223 B2
(45) Date of Patent: Mar. 31, 2015

(54) RECHARGEABLE LONG-TERM ANTIFUNGAL DENTURE MATERIALS

(75) Inventors: Yuyu Sun, Acton, MA (US); Zhengbing Cao, Bothell, WA (US); Xinbo Sun, Bothell, WA (US)

(73) Assignee: The University of South Dakota, Vermillion, SD (US)

( * ) Notice: Subject to any disclaimer, the term of this patent is extended or adjusted under 35 U.S.C. 154(b) by 0 days.

(21) Appl. No.: 13/579,742

(22) PCT Filed: Feb. 18, 2011

(86) PCT No.: PCT/US2011/025397
§ 371 (c)(1),
(2), (4) Date: Dec. 28, 2012

(87) PCT Pub. No.: WO2011/103397
PCT Pub. Date: Aug. 25, 2011

(65) Prior Publication Data
US 2013/0101963 A1    Apr. 25, 2013

Related U.S. Application Data

(60) Provisional application No. 61/306,219, filed on Feb. 19, 2010.

(51) Int. Cl.
| *A61C 13/08* | (2006.01) |
| *A61C 13/00* | (2006.01) |
| *A61C 19/06* | (2006.01) |
| *A61K 6/083* | (2006.01) |

(52) U.S. Cl.
CPC .................. *A61C 13/08* (2013.01); *A61C 13/00* (2013.01); *A61C 19/063* (2013.01); *A61K 6/083* (2013.01)

USPC .......................................................... 433/202.1

(58) Field of Classification Search
CPC ....... A61K 6/083; A61K 31/155; A61K 6/08; A61K 31/4174; A61C 13/00; A61C 19/063; A61C 19/06; C08L 39/06
USPC ........... 433/202.1; 424/422, 423, 435, 49, 50; 435/29
See application file for complete search history.

(56) References Cited

U.S. PATENT DOCUMENTS

| 3,476,854 | A | * | 11/1969 | Molnar | 514/560 |
| 3,956,480 | A | * | 5/1976 | Dichter et al. | 424/54 |
| 4,258,028 | A | * | 3/1981 | Miller, Jr. | 424/49 |
| 4,315,779 | A | * | 2/1982 | Heyd et al. | 106/35 |
| 5,116,603 | A | * | 5/1992 | Friedman | 424/53 |

(Continued)

FOREIGN PATENT DOCUMENTS

| CA | 0884854 A | 2/1971 |
| WO | WO 9961491 A1 * | 12/1999 |

OTHER PUBLICATIONS

International Search Report and Written Opinion issued in PCT/US2011/025397, dated Jun. 12, 2012, 9 pages.

*Primary Examiner* — Cris L Rodriguez
*Assistant Examiner* — Mirayda A Aponte
(74) *Attorney, Agent, or Firm* — Faegre Baker Daniels LLP (57) ABSTRACT

Polymers and copolymers including a functional polymer component may be used as conventional denture materials. Antifungal materials may be releasably bound to the functional polymer component such that the antifungal materials may be slowly eluted over an extended period of time to combat a fungal infection.

7 Claims, 5 Drawing Sheets

(56) References Cited

U.S. PATENT DOCUMENTS

| | | | |
|---|---|---|---|
| 5,160,737 A * | 11/1992 | Friedman et al. | 424/401 |
| 5,270,032 A * | 12/1993 | Pollock et al. | 424/49 |
| 5,486,503 A * | 1/1996 | Oppenheim et al. | 514/3.3 |
| 5,631,228 A * | 5/1997 | Oppenheim et al. | 435/12 |
| 5,639,795 A * | 6/1997 | Friedman et al. | 514/772.6 |
| 5,646,119 A * | 7/1997 | Oppenheim et al. | 514/2.4 |
| 5,648,399 A * | 7/1997 | Friedman et al. | 514/772.6 |
| 5,665,332 A * | 9/1997 | Mundschenk et al. | 424/49 |
| 5,912,230 A * | 6/1999 | Oppenheim et al. | 514/1.4 |
| 6,124,374 A * | 9/2000 | Kolias et al. | 523/120 |
| 2003/0086878 A1* | 5/2003 | Rajaiah et al. | 424/49 |
| 2004/0131558 A1* | 7/2004 | Hauck | 424/49 |
| 2004/0219190 A1* | 11/2004 | Kosti | 424/449 |
| 2005/0054583 A1* | 3/2005 | Wang et al. | 514/21 |
| 2007/0122362 A1* | 5/2007 | Giniger et al. | 424/53 |
| 2010/0210745 A1* | 8/2010 | McDaniel et al. | 521/55 |

* cited by examiner

Please replace Figure 1 with the following Figure 1:

RECHARGEABLE LONG-TERM ANTIFUNGAL DENTURE MATERIALS

RELATED APPLICATION

This application claims the benefit of U.S. Provisional Application Ser. No. 61/306,219 filed Feb. 19, 2010 and entitled "RECHARGEABLE LONG-TERM ANTIFUNGAL DENTURE MATERIALS," said application is incorporated by reference herein in its entirety.

STATEMENT REGARDING FEDERALLY SPONSORED RESEARCH OR DEVELOPMENT

This invention was made with United States Government Support awarded by the National Institutes of Health under grant number 5R03DE018735-02. The United States Government may have certain rights in this invention.

BACKGROUND

In some cases, dentures are beneficial to the nutritional status, speech, appearance, and quality of life of patients who are missing some or even all of their teeth. However, colonization and biofilm formation of *Candida alibicans* on denture materials can lead to *Candida*-associated denture stomatitis (CADS), which is a non-specific inflammatory reaction to microbial antigens, toxins and enzymes that are produced by the colonizing microorganisms.

CADS is a common, recurring disease that affects up to 67% of denture wearers. Factors such as poor oral hygiene, high carbohydrate intake, reduced salivary flow, continuous denture wearing, ageing, malnutrition, immunosuppression, radiation therapy, diabetes mellitus, and possibly treatment with antibiotics are known to increase susceptibility to CADS. In healthy individuals, CADS can be readily controlled. However, for patients who are debilitated, immunocompromised or suffering from systemic diseases, CADS may become a chronic condition; further, the colonized *Candida alibicans* and other species can cause caries, root caries, periodontal diseases, oral and systemic (e.g., gastrointestinal and pleuropulmonary) infections, and even death.

Management of CADS includes denture cleaning and disinfection, appropriate denture wearing habits, use of tissue conditioners or soft liners, and topical or systemic antifungal therapy. However, none of these methods can completely prevent or eliminate *Candida alibicans* colonization and biofilm formation, and the reinfection rate is high, particularly in those who are immunocompromised or medically compromised.

Since CADS is closely associated with *Candida alibicans* colonization and biofilm formation, the use of antifungal dentures can be an attractive option to control the disease. The general principle for fabricating antifungal dentures is to impregnate denture materials with antifungal drugs that elute from the device and impair microbial growth. A high antifungal concentration is reached (at least initially) in the near vicinity of the denture surface, generally exceeding the minimum inhibition concentration (MIC) and fungicidal concentration (MFC) required for susceptible species. The effectiveness and safety of these antifungal dentures for short-term use (e.g., days to weeks) have been confirmed in a number of studies.

However, most of the current antifungal denture materials cannot control CADS for long durations. The major challenge for long-term use of antifungal dentures is the lack of strategies to incorporate enough antifungal drugs into the prostheses and control antifungal drug release rate. The simplest method is to directly add antifungal agents into denture materials. In this approach, however, drug content is generally low, primarily because high drug content could damage the physical properties of the dentures.

Further, because the drugs are simply dispersed in dentures and there are no specific interactions to "hold" them, antifungal agents are released rapidly, in the first several hours or days. To introduce specific interactions, new polymer materials bearing anionic functional groups in the side chains have been synthesized, and these can bind and then slowly release antifungal agents. This method reduces the release rate, but antifungal duration is not improved because of the low amount of antifungal drugs absorbed.

In addition to short antifungal durations, the pattern of release of antifungal drugs needs further optimization. Current systems release antifungal drugs at a decreasing rate over time, regardless of whether colonization or infections are present. If the prostheses could respond to the presence of microbes or infections and initiate or stop drug release accordingly, their effectiveness in controlling CADS would be significantly improved. Unfortunately, this has not been achieved in practice.

Moreover, while drug combination, drug change or drug rotation can be a powerful tool to enhance inhibitory potency and reduce microbial drug resistance in the treatment of fungal infections, this method has not been adopted in the development of antifungal dentures. Rather, current systems normally use one or two antifungal agents, and once the antifungal dentures are fabricated, the structures and quantities of antifungal agents in the dentures are fixed, and cannot be changed in real applications even if the disease/patient's conditions warrant such changes.

SUMMARY

In some embodiments, the invention pertains to an antimicrobial dental prosthesis that includes a polymeric substrate having a functional polymer component. An antifungal agent (which can be a single antifungal agent or a combination of two or more antifungal agents) is releasably bound to the functional polymer component such that the antifungal agent is slowly eluted from the functional polymer component over an extended period of time.

In some embodiments, the invention pertains to a method of reducing a fungal infection in a patient having a rechargeable polymeric dental prosthesis. Once a fungal infection has been detected in the patient, the rechargeable polymeric dental prosthesis is charged with an antifungal agent (a single antifungal agent or a combination of two or more antifungal agents). The antifungal agent is eluted from the dental prosthesis over an extended period of time. Once the fungal infection has been sufficiently reduced, any remaining antifungal agent may be removed.

DETAILED DESCRIPTION

In some embodiments, functional polymers may be covalently bound onto conventional denture materials. In some embodiments, functional polymers may be copolymerized with other polymer materials forming the denture material. In this, a functional polymer may be defined as a polymer that can bind and then slowly release antifungal agents over an extended period of time.

In some embodiments, the functional polymer may be an anionic polymer that forms ionic bonds with cationic antifungal drugs. In some embodiments, a polymer such as PVP may form dipole-dipole interactions with polar antifungal drugs. A polymer such as PVP may undergo hydrogen bonding with an antifungal drug that can donate a hydrogen atom. In some embodiments, the functional polymer may form Vander Waals interactions with the antifungal agents. Illustrative but non-limiting examples of suitable polymers include polyacrylic acid (PAA) and poly(methacrylic acid) (PMAA), and/or polymers containing pyrrolidone groups such as polyvinylpyrrolidone (PVP) may be covalently bound onto or copolymerized with conventional denture materials.

In some embodiments, the antifungal agent may be a single antifungal agent or a combination of two or more antifungal agents. An illustrative but non-limiting example of a suitable antifungal agent is miconazole. Another illustrative but non-limiting example of a suitable antifungal agent is chlorhexidine gluconate.

As will be appreciated, these embodiments provide a multitude of advantages and benefits. For example, in some cases, a polymer including acid groups or pyrrolidone groups may be coated or grafted onto or otherwise secured to the dentures or similar dental prostheses. When no infection is present, the dentures may be used without addition of an antifungal agent. If an infection such as a CSDS infection is found, the dentures may be charged with an appropriate antifungal agent. Once the infection has been eliminated, the antifungal agent may be quenched or otherwise removed from the denture material. In some embodiments, the antifungal agent may exhibit long term release and may be rechargeable. In some cases, the antifungal agent may be switched to a different antifungal agent to, for example, better fight a particular infection.

In some embodiments, such as for high-risk patients, a dental prosthesis such as a denture that has been coated with a polymer such as poly(acrylic acid) may be worn as a conventional denture if no infection such as a CADS infection is present. If CADS occurs, the dentures can be charged with one or more antifungal drugs. Once the complications are cleared, the drug-containing dentures can be washed with a quenching solution, which will compete with the covalently bound poly(acrylic acid) molecules on the dentures for the cationic antifungal drugs. Several cycles of such treatments will "wash out" the bound drugs to quench the therapeutic effects when no further drug release is needed, and the device can be continually used as a conventional denture. If CADS recurs, drugs can be recharged to re-initiate the treatment.

Figure 1:
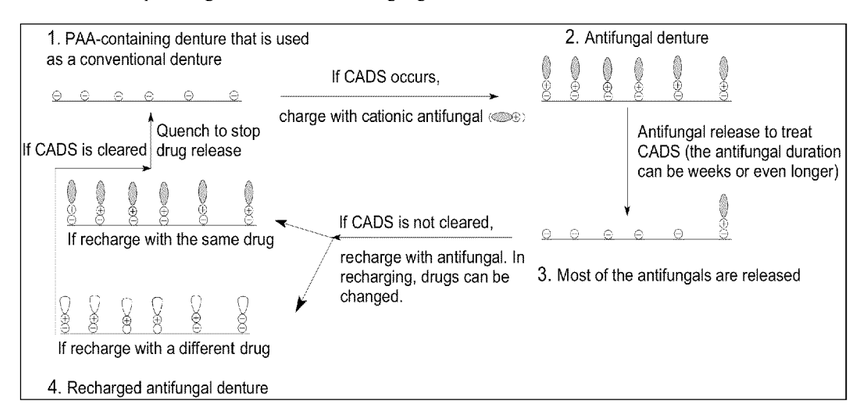
FIG. 1. The PAA based rechargeable click on/click-off antifungal denture approach.

The whole process is schematically shown in FIG. 1. In some embodiments, as shown, the antifungal drug is cationic, and thus may be ionically bonded to the anionic polymer. In some embodiments, as illustrated in FIG. 1, the negatively charged polymer will form ionic complexes with the cationic antifungal drugs. In other embodiments, as referenced above, polymers such as PVP (polyvinylpyrrolidone) can form strong dipole-dipole interactions, hydrogen bonding and/or Vander Waals interactions with the antifungal agents. The strong interactions will "hold" the drugs onto the denture and release them gradually, achieving sustained drug-releasing effects (e.g., weeks to months). This unique click-on/click-off antifungal drug delivery technology offers considerable flexibility for managing recurring CADS and other related diseases.

In some embodiments, the functional polymer is covalently bound onto the dentures, and therefore it will not migrate away with the drugs. Thus, if CADS is not cleared after the first charging, the released drugs can be repeatedly recharged through ionic complex formation (see FIG. 1), dipole-dipole interactions, hydrogen bonding and/or Vander Waals interactions, opening up significant opportunities to achieve long-term therapeutic effects in managing serious CADS and other dental complications. In some embodiments, the antifungal drugs are recharged when the denture or other dental appliance is not in use inside a patient's mouth.

In some embodiments, various classes of antifungal drugs can be combined into one system in the initial charging, and these can be changed and/or switched in subsequent recharging treatments. In some instances, this feature will significantly enhance inhibition potency, reduce toxicity, minimize the risk of developing drug resistance, and offer considerable flexibility in responding to clinical disease status and/or patients' needs.

While the usefulness of the invention is described herein with respect to dental appliances such as dentures, it will be appreciated that the invention may be applicable to a variety of medical devices or different infection protective or treatment devices.

EXAMPLES

Example One

In this example, 10 wt % of acrylic acid (the monomer for preparation of glass ionomers) was copolymerized with urethane dimethacrylate (UDMA) in the curing step to produce denture resins. Denture material discs (13 millimeter diameter, 1 millimeter thick) were prepared by free radical co-polymerization of acrylic acid (AA) and UDMA in aluminum molds. Polymerization was carried out in a laboratory heat-curing unit at 70° C. for 3 hours. The specimens were visually examined to ensure they were free of voids.

Resin discs so formed were immersed in 2% miconazole ethanol solutions at room temperature overnight while UDMA discs without acrylic acid served as controls. The resulting discs were thoroughly washed with distilled water to remove unbound drugs, dried under vacuum, and extracted with ethanol using an automatic soxhlet extraction apparatus to remove the bound drugs so as to determine the quantity of bound miconazole by measuring the absorbance at $\lambda=220$ nm using a UV-VIS spectrophotometer.

The control discs, lacking acrylic acid, were found to have absorbed 8.2±0.7 µg/cm² of miconazole (n=5). After immersing in artificial saliva at 37° C. for 3 days and changing the immersion solution daily, all the absorbed drugs were released, suggesting that the original UDMA resins have low drug binding capability and short drug releasing duration. In contrast, the UDMA discs that were copolymerized with 10 wt % of acrylic acid exhibited a dramatically increased binding capacity of 59.8±2.5 µg/cm² (n=5). It is believed that this is the result of formation of ionic complexes between the acrylic acid component of the copolymer and the miconazole.

Example Two

In this example, a functional polymer containing carboxylate groups was coated onto polymethacrylate resin to produce denture resins. In particular, 10% of poly(methyl methacrylate-co-methacrylic acid) (MMA-co-MAA), which was purchased from Aldrich, with a methyl methacrylate:methacrylic acid feed ratio of 1:0.016, and a molecular weight of 34,000, was dissolved in ethanol. Acrylic denture resin formulations (Lucitone 199) were purchased from Dentsply Intl, to represent conventional PMMA-based heat-polymerizing acrylic resins, which are commonly used for the fabrication of denture bases. Based on the manufacturer's formula, the monomer was mixed with the powder, resin and discs (13 mm diameter) were fabricated aseptically following the manufacturer's recommendations (90 min at 73° C. and then 100° C. boiling water for 30 min). The specimens were visually examined to ensure they are free of voids.

The MMA-co-MAA solution was coated onto the disc with a brush (the weight ratio of the disc to the coating solution was 10:1). The coated discs were left in a fume hood for dry for three days. The discs were than immersed in 10% chlorhexidine digluconate (CG) aqueous solution at room temperature overnight. The resulting discs were thoroughly washed with distilled water to remove unbound drugs, dried under vacuum, and extracted with water using an automatic soxhlet extraction apparatus to remove the bound drugs so as to determine the quantity of bound CG by measuring the absorbance at $\lambda=260$ nm using a UV-VIS spectrophotometer.

The control discs (the acrylic disc without coating), lacking the functional polymer, were found to have absorbed 3.2±0.1 µg/cm² of CG (n=5). After immersing in artificial saliva at 37° C. for 3 days and changing the immersion solution daily, all of the absorbed drugs were released, suggesting that the original acrylic resins have low drug binding capability and short drug releasing duration. In contrast, the acrylic discs that were coated with the functional polymer (MMA-co-MAA) exhibited a dramatically increased binding capacity of 36.7±5.9 µg/cm² of CG (n=5). It is believed that this is the result of formation of strong interactions between the methacrylic acid component of the copolymer and the CG.

Example Three

In this example, a functional polymer containing pyrrolidone groups was coated/grafted onto UDMA resin to produce denture resins. UDMA discs were prepared as in Example 1. A solution containing 8% of UDMA, 12% of vinyl pyrrolidone, and 0.05% of AIBN in acetone was coated onto both sides of the UDMA discs (the weight ratio of the disc to the coating solution was 10:5). The discs were left in a fume hood for 4 hours, and then cured in an oven at 80° C. for 2 hours, and then 100° C. for 2 hours. The discs were than immersed in 5% miconazole ethanol solution at room temperature overnight.

The resulting discs were thoroughly washed with distilled water to remove unbound drugs, dried under vacuum, and extracted with ethanol using an automatic soxhlet extraction apparatus to remove the bound drugs so as to determine the quantity of bound miconazole by measuring the absorbance at $\lambda=220$ nm using a UV-VIS spectrophotometer.

The control discs (UDMA disc without coating/grafting), lacking the functional polymer, were found to have absorbed 7.4±1.2 µg/cm² of miconazole (n=5). After immersing in artificial saliva at 37° C. for 3 days and changing the immersion solution daily, all the absorbed drugs were released, suggesting that the original UDMA resins have low drug binding capability and short drug releasing duration.

In contrast, the UDMA discs that were coated/grafted with the functional polymer containing pyrrolidone groups exhibited a dramatically increased binding capacity of 47.3±3.6 µg/cm² of pyrrolidone (n=5). It is believed that this is the result of formation of strong dipole-dipole interactions, hydrogen bonding, and/or Vander Waals interactions between the pyrrolidone component of the copolymer and the miconazole.

Example Four

Figure 2A:
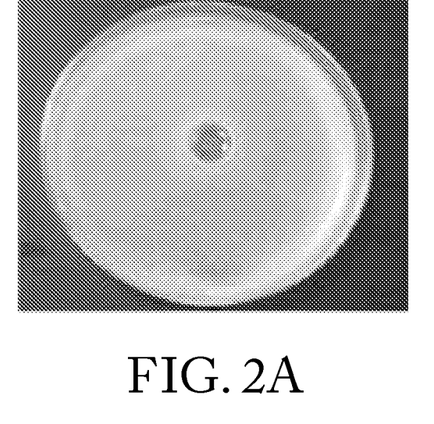
FIG. 2A. Zone of inhibition result of the original UDMA disc.
Figure 2B:
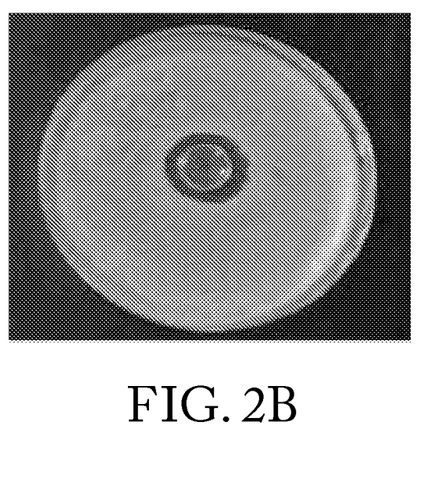
FIG. 2B. Zone of inhibition result of PAA-based UDMA disc containing 59.8±2.5 µg·cm$^2$ of miconazole.

The antifungal effects of the discs from Example 1 containing 59.8±2.5 µg/cm² of miconazole were tested with a zone of inhibition study, and the original UDMA discs were used as controls. Briefly, the control and drug-containing discs were individually placed onto YM agar plates inoculated with 5.3×10⁶ CFU/mL of *Candida alibicans* (ATCC 10231). The plates were then incubated at 37° C. for 48 hr. As shown in FIG. 2 A, the control disc did not show any inhibition zone. The miconazole-containing disc, however, provided a clear zone of 5.0±0.4 mm (FIG. 2 B), indicating potent antifungal effects.

Example Five

To test anti-biofilm activity, PAA-based UDMA discs containing 59.8±2.5 µg/cm2 of miconazole prepared in Example One were immersed in 10 mL 5.3×10⁶ CFU/mL of *Candida alibicans* YM broth suspensions at 37° C. with constant shaking (the original UDMA resin discs as controls). SEM study showed that after one day of incubation, scattered *Candida alibicans* cells adhered to the original UDMA discs (FIG. 3 A), and after three days, the disc surfaces were covered with layers of colonized *Candida alibicans* (FIG. 3 B), suggesting biofilm formation. On the other hand, the PAA-based drug-containing discs showed much clearer surfaces, and no adherent cells/biofilm could be observed (FIGS. 3 C and 3D).

Example Six

Figure 4A:
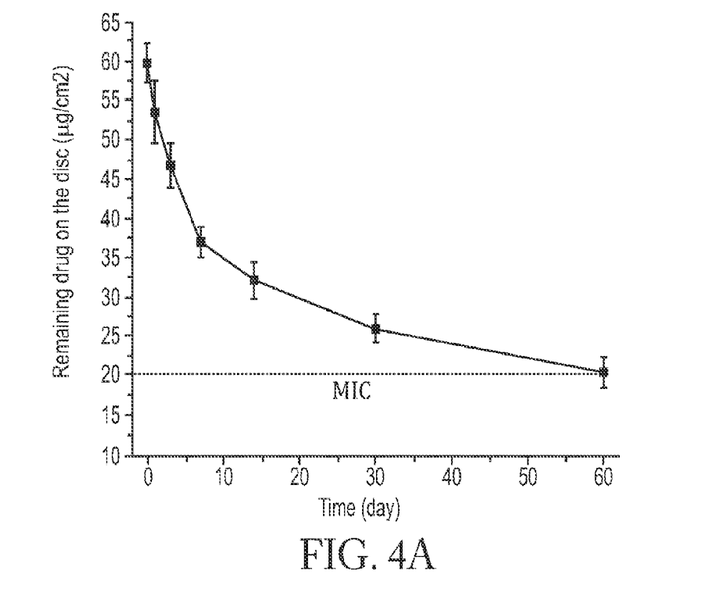

In order to determine the antifungal duration, a series of freshly prepared PAA-based UDMA discs prepared by the process of Example One containing 59.8±2.5 µg/cm2 of miconazole were immersed individually in 10 mL artificial saliva at 37° C. under constant shaking (60 rpm). The immersion solution was changed daily, and the concentration of the released miconazole was determined by UV-VIS analysis at 220 nm. As shown in FIG. 4A, the bound miconazole showed sustained releasing behavior. After 7 days of release, the disc surface contained 37.1±2.2 µg/cm² of miconazole; after 14 days of release, 32.1±2.5 µg/cm² of miconazole remained on the disc surface; after 30 days, the remaining drug content was 25.96±1.8 µg/cm²; and even after 60 days, the disc still had 20.4±2.1 µg/cm² of bound drug (n=5).

Figure 3A:
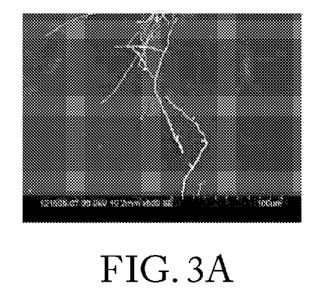
FIG. 3A. SEM results of the original UDMA disc after immersing in *C. albicans* for 1 day.
Figure 3B:
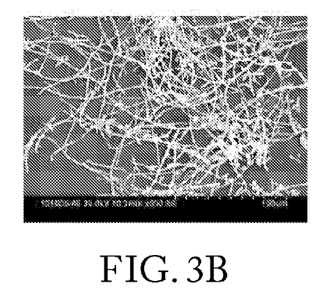
FIG. 3B SEM result of the original UDMA disc after immersing in *C. albicans* for 3 days.
Figure 3C:
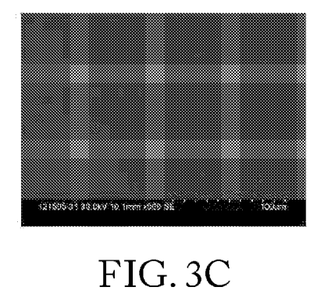
FIG. 3C SEM result of PAA-based disc containing 59.8±2.5 µg/cm² of miconazole after immersing in *C. albicans* for 1 day.
Figure 3D:
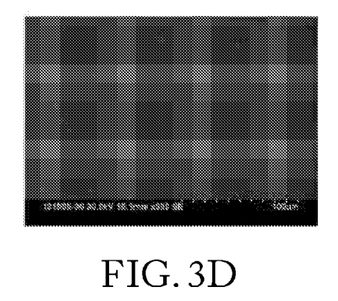
FIG. 3D SEM result of PAA-based disc containing 59.8±2.5 µg/cm² of miconazole after immersing in *C. albicans* for 3 days FIG. 4A. Elution curve of miconazole from the PAA-based UDMA discs. The original miconazole content was 59.8±2.5 µg/cm².
Figure 4B:
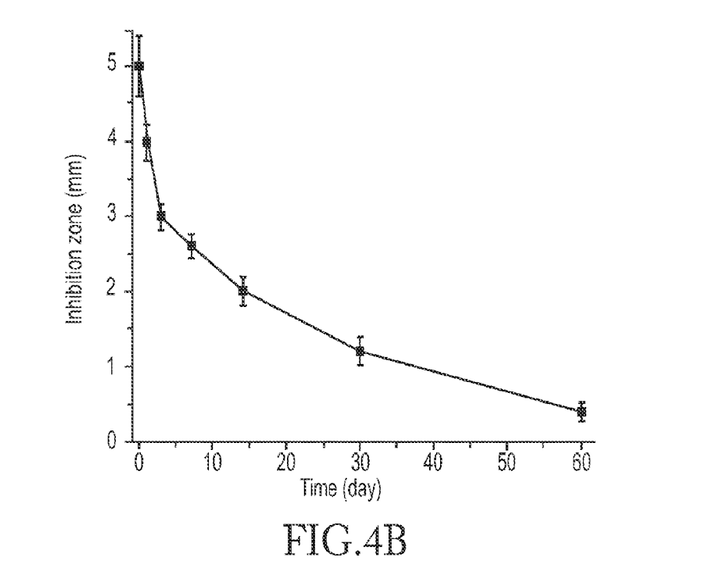
FIG. 4B. Effects of drug releasing periods on inhibition zone size against the test *Candida* cells.

Parallel to the above-mentioned releasing study, periodically, some of the discs were taken out of the immersion solution and submitted to zone of inhibition tests to determine the effects of drug release on antifungal potency. As shown in FIG. 4 B, the inhibition zone size decreased with the increase of releasing periods (and thus the decrease of remaining drug content on the discs): after 7 days of release, the inhibition zone decreased from 5.0±0.4 mm (see FIG. 3 B) to 2.6±0.16 mm (n=5); after 14 days of release, the inhibition zone was 2.0±0.2 mm; after 30 days, the zone was 1.2±0.15 mm; and after 60 days, the zone size was 0.4±0.1 mm. At even longer releasing periods, the discs could not provide any inhibition zones, suggesting that 25.96±1.8 µg/cm$^2$ was the minimum inhibition content (MIC) of bound miconazole on the discs that could provide an inhibition zone against the testing *Candida alibicans* cells.

Example Seven

At the end of the 60-day release study, the discs were again treated with 2% miconazole ethanol solutions at room temperature overnight. After extraction with an automatic soxhlet extraction apparatus, UV-VIS study showed that the recharged discs contained 62.1±3.2 µg/cm$^2$ miconazole, which could generate an inhibition zone of 5.2±0.6 mm against the test *Candida alibicans* (n=5). The release pattern of miconazole from the drug-containing discs was resumed, and the effects of drug releasing periods on inhibition zone size against the test *Candida alibicans* cells were essentially unchanged, suggesting that the released drugs could be fully recharged to regenerate the original antifungal effects.

Example Eight

In recharging, miconazole could be changed to other cationic antifungal drugs. In this study, after 60 days of miconazole release, the discs prepared in Example One were thoroughly washed with distilled water, airdried, and then immersed in 5 wt % of chlorhexidine gluconate (CG) aqueous solutions at room temperature overnight (the original UDMA resins served as controls). The resulting discs were thoroughly washed with distilled water to remove unbound drugs, air-dried, and extracted with distilled water using an automatic soxhlet extraction apparatus to remove the bound CG. CG content in the extraction solution was determined by UV-VIS spectrophotometer at 2=260 nm. No detectable CG could be extracted from the original UDMA discs. The PAA-based discs, however, contained 45.73±2.1 µg/cm$^2$ of CG (n=5). In the antifungal duration and zone of inhibition tests (see Examples 2-4 for experimental details), the new CG-containing discs showed shorter antifungal duration and smaller inhibition zones than the original miconazole-containing discs, as shown in FIG. 5.

Figure 5A:
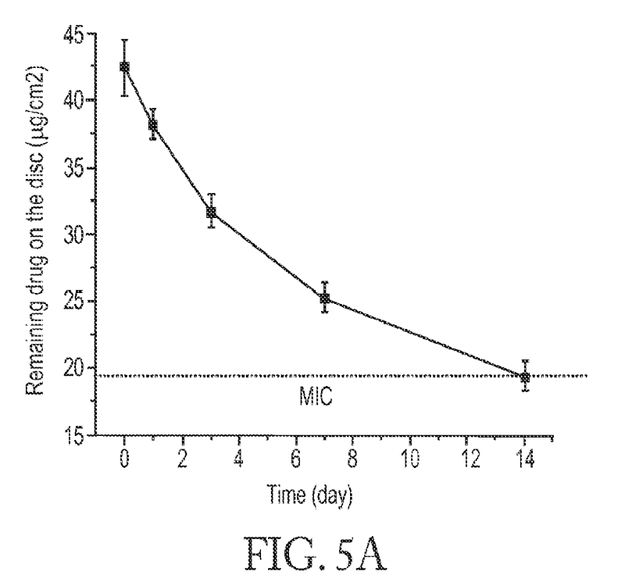
FIG. 5A. Elution curve of PAA-based UDMA discs recharged with 45.73±2.1 µg/cm² of CG.
Figure 5B:
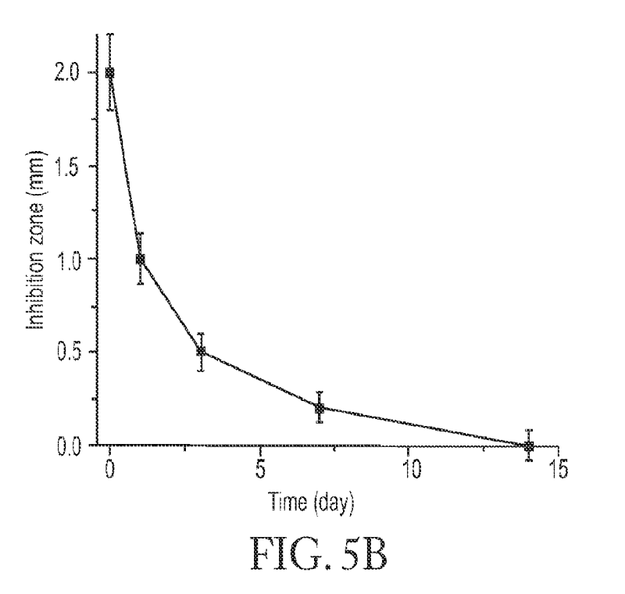
FIG. 5B. Effects of drug releasing periods on inhibition zone size against the test *Candida* cells.

After 1 day of release, the CG content on the recharged discs decreased from 45.73±2.1 µg/cm$^2$ to 38.15±1.0 µg/cm$^2$, and the discs generated an inhibition zone of 2.0±0.2 mm (n=5, FIGS. 5 A and 5 B). After 7 days of release, the discs contained 25.11±0.6 µg/cm$^2$ of CG, and the inhibition zone size was 0.2±0.05 mm. When the release period was extended to 14 days, although the discs still contained 19.55±0.3 µg/cm$^2$ of CG, no clear inhibition zone against the test *Candida alibicans* cells could be detected. These phenomena could be caused by the high water solubility (and thus faster drug release) and relatively low antifungal potency of CG. Nonetheless, after 14 days of release, the discs were recharged again with 5 wt % of CG aqueous solutions at room temperature overnight; >96% of the original CG was recharged, and the drug release behavior and zone of inhibition capability were again regenerated.

Example Nine

Biocompatibility of the PAA-containing resin discs was preliminarily evaluated with the trypan blue assay against bald/c mouse 3T3 fibroblast cells (ATCC), using both cell-only samples and the original UDMA resin discs as controls. The results are summarized in Table 1.

TABLE 1

Cell viability against bald/c mouse 3T3 fibroblast cells evaluated with the trypan blue assay

| Samples | % of undamaged cells after 1 day | % of undamaged cells after 3 days |
|---|---|---|
| Cell-only control | 98.2 ± 7.7 | 94.8 ± 6.4 |
| Original UDMA resin disc | 90.1 ± 5 | 8 92.1 ± 5.3 |
| UDMA resin disc with 10% of PAA | 89.2 ± 6.2 | 90.9 ± 2.0 |

As demonstrated by the trypan blue assay, the viability of the mouse 3T3 fibroblast cells was not significantly affected by the presence of the UDMA resin disc with 10% of PAA after 3 days of contact. Of all the cells exposed to the PAA-based resins, only a few had trypan blue-stained nuclei (indicating cell death), and when viewed by phase-contrast microscopy, the stained cells were of the same size and shape as the unstained cells (images not shown). Cultures of the cells exposed to the original UDMA resin discs and PAA-based UDMA discs showed similar percentages of stained cells and intact cellular morphology, and there were no significant differences (95% of confidence level) in the proportions of trypan blue-stainable cells in cultures exposed for 3 days between the controls and the test group, pointing to good biocompatibility of the PAA-containing experimental resins.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The invention claimed is:

1. A method of personalized managing a fungal infection in a patient having a click-on/click-off rechargeable polymeric dental prosthesis, the method comprising steps of:
   detecting a fungal infection in the patient;
   charging the click-on/click-off rechargeable polymeric dental prosthesis with at least one antifungal agent;
   eluting the antifungal agent from the dental prosthesis over an extended period of time; and
   removing any remaining antifungal agent by a quenching solution of by agents that can form interactions with the bound drug through ionic interactions, dipole-dipole interactions, Vander Waal interactions, hydrogen bonding, and/or hydrophobic interactions once the fungal infection has been sufficiently reduced.

2. The method of claim 1, wherein the fungal infection comprises a *Candida albicans* infection.

3. The method of claim 1, wherein eluting the antifungal agent from the dental prosthesis over an extended period of time comprises eluting an antifungal-effective amount of the antifungal agent for a period of at least about 7 days.

4. The method of claim 1, wherein the antifungal-effective amount of the antifungal material is sufficient to provide a minimum inhibition concentration and/or minimum fungicidal concentration within an area proximate the dental prosthesis.

5. The method of claim 1, further comprising a step of re-charging the click-on/click-off rechargeable polymeric dental prosthesis with a second antifungal agent that targets the remaining fungal infection.

6. The method of claim 5, wherein the second antifungal agent is the same antifungal agent used for the initial charging.

7. The method of claim 5, wherein the second antifungal agent is different from that used for the initial charging.

* * * * *

UNITED STATES PATENT AND TRADEMARK OFFICE
CERTIFICATE OF CORRECTION

PATENT NO.        : 8,992,223 B2
APPLICATION NO.   : 13/579742
DATED             : March 31, 2015
INVENTOR(S)       : Sun et al.

Page 1 of 1

It is certified that error appears in the above-identified patent and that said Letters Patent is hereby corrected as shown below:

In the Specification

At Column 1 delete Lines 15 - 18 and insert:
--This invention was made with government support under grant number 5R03DE018735-02 awarded by the National Institutes of Health. The government has certain rights in the invention.--

Signed and Sealed this
First Day of January, 2019

Andrei Iancu
*Director of the United States Patent and Trademark Office*